United States Patent [19]

Immel et al.

[11] Patent Number: 5,166,440
[45] Date of Patent: Nov. 24, 1992

[54] PROCESS FOR THE PREPARATION OF N-ALKYLATED AROMATIC AMINES

[75] Inventors: Otto Immel, Krefeld; Helmut Waldmann, Leverkusen; Rudolf Braden, Odenthal, all of Fed. Rep. of Germany

[73] Assignee: Bayer Aktiengesellschaft, Leverkusen, Fed. Rep. of Germany

[21] Appl. No.: 626,343

[22] Filed: Dec. 12, 1990

[30] Foreign Application Priority Data

Dec. 21, 1989 [DE] Fed. Rep. of Germany ....... 3942413
Mar. 15, 1990 [DE] Fed. Rep. of Germany ....... 4008257

[51] Int. Cl.$^5$ ............................................ C07C 209/02
[52] U.S. Cl. .................................... 564/401; 564/399; 564/408; 564/428; 558/418; 558/419
[58] Field of Search ...................... 564/399, 401, 428; 558/418, 419

[56] References Cited

U.S. PATENT DOCUMENTS

| | | | |
|---|---|---|---|
| 3,957,874 | 5/1976 | Dockner et al. | 558/418 |
| 4,721,810 | 1/1988 | Hargis | 564/399 |
| 4,906,782 | 3/1990 | Hara et al. | 564/478 |
| 4,921,980 | 5/1990 | Rusek | 564/401 |
| 4,927,931 | 5/1990 | Molzahn et al. | 544/357 |

Primary Examiner—Richard L. Raymond
Assistant Examiner—Brian M. Burn
Attorney, Agent, or Firm—Sprung, Horn, Kramer & Woods

[57] ABSTRACT

Aromatic amines, alkylated on the N-atom, can be prepared by catalytic alkylation of aromatic amines with alcohols or the corresponding ethers or by transalkylation with aromatic amines alkylated on the N-atom, whereby niobic acid or tantalic acid is used as the catalyst.

20 Claims, No Drawings

PROCESS FOR THE PREPARATION OF N-ALKYLATED AROMATIC AMINES

BACKGROUND OF THE INVENTION

1. Field of the Invention

The present invention relates to a process for the preparation of N-alkylated anilines by reaction of anilines with lower alcohols or by reaction with anilines alkylated on the N-atom (transalkylation) in the presence of niobic acid or tantalic acid at elevated temperature.

N-Alkylated aromatic amines, which can be prepared according to the invention, are starting materials for the preparation of dyestuffs, pesticides, urethanes, pharmaceuticals, plant protection agents and the like. They are also used as mineral oil additives and as additives for surface coatings or other polymeric systems.

2. Description of the Related Art

Various processes for the preparation of secondary and tertiary aromatic amines are known. In general, they are prepared by alkylation of anilines with alcohols in the presence of acidic catalysts. Thus, it is already known, for the preparation of N-alkylated aromatic amines, to react aromatic amines with alkanols or the corresponding dialkyl ethers in the gas phase. For example, alumina or silicates are proposed as catalysts (for example silicates, such as Tonsil, in German Patent Specification No. 638,756). The said catalysts have the disadvantage that their activity decreases rapidly in the alkylation of aromatic amines (Houben-Weyl, Methoden der org. Chemie [Methods of organic chemistry], Volume XI/1 (1957) page 126).

It is also known from German Patent Specification No. 617,990 and DE-OS (German Published Specification) No. 2,335,906 that support materials which contain oxygen acids of phosphorus can be used for the said task. However, the service life and selectivity of such catalysts are not satisfactory for industrial processes.

Moreover, it was proposed in U.S. Pat. No. 2,580,284 to react aniline and methanol, using a catalyst which contains metallic copper on $Al_2O_3$ and further oxides, such as zinc oxide, cadmium oxide, iron oxide, chromium oxide, calcium oxide, magnesium oxide or potassium oxide. Such catalysts suffer from the deposition of tarry substances even after a relatively short time. A further process for reacting aniline with methanol to give N-methylaniline according to DE-OS (German Published Specification) No. 2,061,709 is carried out on a chromium catalyst which can contain copper, zinc, iron, nickel or molybdenum as well as barium, magnesium or manganese. This process has the disadvantage that it is carried out under a pressure of 50-150 bar and is therefore too expensive for industrial application; this catalyst also does not reach a satisfactory service life.

According to DE-OS (German Published Specification) No. 2,120,641, copper chromite catalysts with barium, manganese, cerium and other elements as promoters are used for the preparation of secondary or tertiary aromatic amines from aliphatic alcohols and aromatic nitro compounds. However, this process leads to unsatisfactory yields.

Only a few and unsatisfactory processes are available for the preparation of anilines dialkylated on the N-atom, particularly for the preparation of N,N-diethylaniline.

In addition, it is in general desirable to be able, on the same catalyst, to set variable ratios of N-monoalkyl anilines to N,N-dialkyl anilines as required.

In U.S. Pat. No. 4,599,449, a process for the gas phase alkylation of aromatic amines with alcohols on transition metal oxides of subgroup 8 of the periodic table of the elements is described. However, the yield of alkyl anilines is very low. Even with a 5-fold excess of ethanol, the conversion of the aniline remains very low at a maximum of 38 %, and N,N-diethylaniline is obtained only in an inadequate yield. Furthermore, the proportion of ringalkylated by-products is very high in this process.

DE-OS (German Published Specification) No. 2,335,906 teaches the alkylation of arylamines with alcohols on silica catalysts which are coated with 0.1 to 20% by weight of phosphoric acid. To obtain good selectivities, however, a very large excess of alcohol of up to 20 mol equivalents is required. This has, on the one hand, the consequence of a low space-time yield and, on the other hand, the separation and recycle of the excess alcohol involves a high distillation cost. In order to avoid rapid deactivation of the catalyst and to ensure a long service life of the catalyst, it is necessary, furthermore, to feed phosphoric acid and/or phosphoric acid alkyl esters continuously during the alkylation; part of these phosphorus compounds is, however, always discharged and contaminates the reaction product, necessitating expensive separations.

It is also to use zeolites as catalysts for the gas phase alkylation of aromatic amines with alcohols. In U.S. Pat. No. 4,801,752, zeolites of the ZSM 5 type having an $SiO_2/Al_2O_3$ ratio of 20–700 are proposed. Flexible control of the yield in the direction of N,N-diethylaniline, is however, possible only to a certain extent. Under the most favourable conditions, a maximum molar selectivity of 10.1% for N,N-diethylaniline is achieved. Moreover, temperatures of up to more than 400° C. must be applied in this process. In addition, a significantly large proportion of unidentified ring-alkylated by-products is formed.

U.S. Pat. No. 4,613,705 describes the alkylation of aromatic amines in the presence of a catalyst which is composed to the extent of at least 70% of a transition metal oxide from group V B of the periodic table of the elements and to the extent of up to 30% of tin (IV) oxide, for example $V_2O_5/SnO_2$, $Nb_2O_5/SnO_2$ and $Ta_2O_5/SnO_2$. However, the conversion of aromatic amine is low, as is the selectivity for N,N-diethylaniline. By contrast, the proportion of undesired by products is very high. Therefore metal oxides of groups V B of the periodic table of the elements seemed to be unsuitable catalysts for the N-alkylation of anilines in general, and especially for the preparation of N-ethyl and N,N-diethyl anilines and in particular for the preparation of N-ethyl aniline.

It was therefore the object of the present invention to overcome the abovementioned disadvantages and to provide a technically feasible, more economical process for the preparation of N-alkylated anilines.

SUMMARY OF THE INVENTION

It has now been found that aromatic amines alkylated on the N-atom can be prepared from aromatic amines and low alcohols if the reaction is carried out in the presence of niobic acid or tantalic acid.

Preferably, the invention relates to a process for the preparation of aromatic amines of the formula

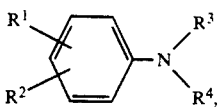 (I)

wherein $R^1$ and $R^2$ independently of one another can denote hydrogen or straight-chain or branched $C_1$–$C_5$-alkyl or $C_1$–$C_5$-alkoxy, fluorine, chlorine, bromine or cyano or also a fused benzene ring which can be substituted by methyl, ethyl, methoxy or ethoxy, and $R^3$ and $R^4$ independently of one another represent straightchain or branched $C_1$–$C_{10}$-alkyl or $C_3$–$C_{10}$-cycloalkyl, it being additionally possible for $R^4$ to represent hydrogen, by reacting aromatic amines of the formula

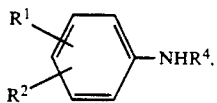 (II)

with alkanols of the formula

 (III), $R^3OH$ or the corresponding ethers of the formula

 (IV)

$R^3$-O-$R^3$ $R^1$, $R^2$, $R^3$ and $R^4$ having the above meaning, or by reacting aromatic amines of the formula

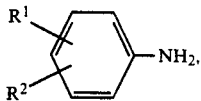 (V)

with aromatic amines of the formula

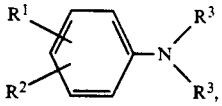 (VI)

$R^1R^2$ and $R^3$ having the above meaning, in the gas phase or liquid phase at an elevated temperature, which is characterized in that the reaction is carried out in the presence of niobic acid or tantalic acid at 160°–400° C., preferably at 200°–300° C.

DETAILED DESCRIPTION OF THE INVENTION

In particular, there was a demand for having a catalytic process available, by means of which a large number of differently substituted anilines can be dialkylated, in particular diethylated, on the N-atom in the gas phase and which does not show the said disadvantages; the alkyl radicals should in particular be those having more than one C atom. The catalysts should be distinguished by ready availability and high service lives and ensure high conversions at good selectivity of the N,N-dialkylation, in particular of the N,N-diethylation.

These demands in connection with the dialkylation are met when niobic acid or tantalic acid (hydrated niobium(V) oxide or hydrated tantalum(V) oxide) is used as the catalyst The novel process ensures the high yields and conversions demanded, there is virtually no ring alkylation, and the catalyst used has service lives of more than 1,000 hours. The catalyst can be regenerated in a manner known per se by burning off with air in the presence of steam.

The invention therefore relates in particular to a process for the preparation of N,N-dialkylanilines, in particular N,N-diethylanilines, by reaction of the underlying anilines with alkanols or dialkyl ethers, in particular ethanol or diethyl ether, at 230°–330° C. in the gas phase under 0.5–3 bar, which is characterized in that a hydrated niobium(V) oxide $Nb_2O_5 \cdot mH_2O$ or a hydrated tantalum(V) oxide $Ta_2O_5 \cdot n\ H_2O$, which has a BET surface area of 5–350 $m^2/g$, preferably 50–350 $m^2/g$, particularly preferably 100–250 and very particularly preferably 100–200 $m^2/g$, is used as the catalyst and aniline and alkanol or diethyl ether are used in a molar ratio of 1:2–10 or 1:1–5 respectively.

It is an essential feature of the process according to the invention to employ niobic acid or tantalic acid as the catalyst. As is known, niobic acid is a hydrated niobium pentoxide ($Nb_2O_5 \cdot nH_2O$), which can be obtained, for example, by treating aqueous solutions of niobic acid salts with strong mineral acids or by treating niobic acid halides or niobic acid esters with water or bases. Niobic acid precipitated in this way is dried and then represents a sparingly soluble solid compound, the residual water content of which is not defined, even though a niobic acid prepared in this way externally represents a dry powder. The preparation of niobic acid (hydrated niobium pentoxide) is described for example, in Gmelins Handbuch der Anorganischen Chemie [Handbook of Inorganic Chemistry], 8th edition, Niobium Part B1, page 49.

Hydrated tanalum(V) oxides (tantalic acid) for the preparation of the catalysts to be used according to the invention can be prepared by hydrolysis of tantalum(V) salts, tantalum(V) alcoholates or other suitable hydrolysable tantalum(V) compounds. The hydrolysis can be effected in the known manner by means of dilute acids or dilute alkalis, in many cases also by water alone. The procedure for such a hydrolysis is known in principle to those skilled in the art and is described, for example, in Gmelins Handbuch der Anorganischen Chemie [Handbook of Inorganic Chemistry], 8th edition, Tantalum, Part B1 (1970), page 53 and T. Ushikubo, K. Wada, Chem. Lett. 1988, page 1573.

To enable the hydrated niobium or tantalum(V) oxide to be brought into the lumpy form more suitable for the operation of a fixed-bed gas-phase reactor, the moist precipitate from the hydrolysis is, for example, thoroughly kneaded in a kneader and processed in a granulation apparatus to give shaped particles. The moist shaped bodies are then dried, for example at 120° C., and calcined for 0.5 to 5 hours at 200–400° C., during which the modification preferred for the process according to the invention, having the required BET surface area is formed.

The hydrated niobium or tantalum(V) oxide thus formed has a BET surface area of 5–350 $m^2/g$.

For the preparation of granules, extrudates or beads, the catalyst can also be coated onto a support or pressed with a binder and granulated.

Niobic acid or tantalic acid is, with respect to the process according to the invention, an active substance whose activity is also preserved by mixing with other solids. Examples of suitable solids are titanium dioxide, zinc oxide, magnesium oxide, iron oxide, silicon dioxide, graphite and others. Mixtures of niobic acid or from 5:95 to 99:1, preferably 50:50 to 98:2, can be used, for example. Of course, pure niobic acid or tantalic acid can also be used. For example, niobic acid or tantalic acid can be used pure or as a mixture with inert solids as a powder or in granulated form. The pulverulent form is here more suitable for the liquid-phase process, while the granulated form is suitable for the arrangement as a fixed bed in the gas-phase process. The granulated form can, for example, represent the form of tablets, pellets, small rods or beads. Mixtures of niobic acid and tantalic acid can also be used. In particular, those mixtures can be used which correspond to the particular mixture content in naturally occurring ores.

Niobic acid or tantalic acids or their mixtures with other, in general inert solids can, for activation, also be activated with strong mineral acids, preferably with hydrofluoric acid or sulphuric acid. Such an activation can be carried out, for example, by impregnation. For operation in the liquid phase, niobic acid or tantalic acid is used in a quantity of 2%-25 % by weight, preferably 4%-20 % by weight, relative to the aromatic amine to be alkylated.

The process according to the invention is carried out at a temperature of 160°–400 TM ° C., preferably 200°–330° C., particularly preferably 220°–330° C., and under a pressure of 0.5–100 bar, preferably 3–100 bar in the liquid phase or of 0.5–3 bar in the gas phase. Operation at 200°–330° C. in the gas phase is preferred here.

The catalyst loading LHSV (liquid hourly space velocity) can be varied within the range of 0.1–4 1/l/h, preferably of 0.3–2 1/l/h. The LHSV is here defined as the ratio of the volume of the liquid aniline/alkanol/dialkyl ether mixture per catalyst volume per hour.

The following may be mentioned by way of example as straight-chain or branched $C_1$–$C_5$-alkyl or $C_1$–$C_5$-alkoxy in the abovementioned formulae: methyl, ethyl, propyl, isopropyl, butyl, isobutyl, the various pentyl radicals, methoxy, ethoxy, propoxy, isopropoxy, butoxy, isobutoxy, and the various pentyloxy radicals. Moreover, $C_5$–$C_{10}$-alkyl is, for example, straight-chain or branched hexyl, octyl or decyl. In a preferred manner, methyl, ethyl, methoxy and ethoxy, and particularly preferably methyl and methoxy may be mentioned as such radicals. $C_3$–$C_{10}$-Cycloalkyl is, for example, cyclopropyl, cyclobutyl, cyclopentyl, cyclohexyl, cycloheptyl, cyclooctyl, methylcyclopentyl, methylcyclohexyl, 4-tert.-butyl-cyclohexyl or menthyl, preferably cyclopropyl, cyclopentyl and cyclohexyl.

In a preferred way, the starting materials are aromatic amines of the formula (V), wherein $R^1$ and $R^2$ have the above meaning. In a further preferred form, the starting materials are aromatic amines of the formula

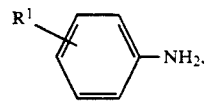

wherein $R^1$ has the above meaning.

A list, which is given by way of example and is by no means exhaustive, of aromatic amines for the process according to the invention is the following: aniline, 1-naphthylamine, o-, m- and p-toluidine, o-, m- and p-ethylaniline, the isomeric xylidines such as 2,3-, 2,4-, 2,5-, 2,6-, 3,4- or 3,5-dimethylaniline and 4-methyl-1naphthylamine. The process according to the invention is particularly important for the alkylation and transalkylation starting from aniline and the toluidines.

When the process according to the invention is carried out in the gas phase, the aromatic amine used as a starting material is in general vaporised before it enters the reaction space and passed over the catalyst arranged as a fixed bed. The vaporised starting material can be diluted with a stream of carrier gas, for example with $H_2$, $N_2$, steam, $CH_4$ and other gases inert in the process according to the invention.

Alkanols for the process according to the invention are open-chain alkanols having 1–10° C. atoms, preferably having 1–6° C. atoms and particularly preferably having 1–2 C atoms, and cyclic alkanols having 3–10 C atoms, preferably having 3, 5 or 6 C atoms, such as methanol, ethanol, propanol, i-propanol, butanol, i-butanol, pentanol, i-pentanol, the isomeric hexanols, heptanols, octanols or decanols, cyclopropanol, cyclobutanol, cyclopentanol, cyclohexanol, cycloheptanol or cyclooctanol, and also 2-, 3- or 4-methyl-cyclohexanol, 2-ethyl-cyclohexanol, 3,3,5-trimethylcyclohexanol, 4-tert.-butyl-cyclohexanol and menthol ($C_{10}$).

In place of the alkanols $R^3OH$ (III), the corresponding ethers $R^3$—O—$R^3$ (IV) can also be used; however, the use of the alkanols is preferred.

In place of the alkanols, the corresponding olefins and water can also be used, for example ethylene and water in place of ethanol, it being possible that the alkanol is formed in a preceding reaction step and reacts further according to the invention with the aromatic amine.

The molar ratio of the alkanol to the aromatic amine to be alkylated on the N-atom is 0.3–20:1, preferably 0.7–15:1 and particularly preferably 0.7–7:1. When the corresponding ethers are used, 1 mol of $R^3$—O—$R^3$ is to be equated with 2 mol of $R^3$—OH for the calculation of the molar ratio.

Using such molar quantities of alkanol, secondary or tertiary aromatic amines of the formula (I) can be prepared from aromatic amines of the formula (II), wherein $R^4$ has the meaning of hydrogen and is accordingly identical with the aromatic amines of the formula (V). Furthermore, tertiary aromatic amines of the formula (I) can also be prepared from secondary aromatic amines of the formula (II), wherein $R^4$ is other than hydrogen. In general, this results in a mixture of secondary and tertiary aromatic amines which, in some cases, may still contain primary aromatic amine if the latter is used as the starting material. Such mixtures can be separated, for example by distillation, in a manner known to those skilled in the art. In many cases, it is desirable to prepare a major proportion of or exclusively secondary aromatic amines which are thus only monoalkylated on the N-atom. In such a case, any tertiary amine (dialkylated on the N-atom) which may also have been formed can be added to the starting mixture of the process according to the invention, unless it can be put to use on its own. The renewed formation of tertiary amines can be suppressed by this addition, or the tertiary amine transfers one of the alkyl groups in a transalkylation reaction to an aromatic amine of the formula (V) which is not substituted on the N-atom. In this case, the quantity of the alkanol or corresponding ether to be used can be reduced. It is likewise possible to start only from an aromatic amine (V) to be alkylated and an aromatic amine of the formula (VI) dialkylated on the N-atom, without additional use of an alkanol or the corresponding ether, and to carry out only the transalkylation described. All these possibilities make the process according to the invention highly variable with respect to the preparation of amines which are monoalkylated or dialkylated on the N-atom.

For the case of the predominantly only mono-N-alkylation, it is also preferred to use an even narrower molar range of 0.8-5 mol of alkanol per mol of primary aromatic amine. The process according to the invention meets the desire for only mono-N-alkylation very well. In fact, it has been found, surprisingly, that almost exclusively aromatic amines monoalkylated on the N-atom are formed even in the case of such relatively high molar quantities of alkanol, namely up to 5 mol per mol of the primary aromatic amine, if the reaction remains within the lower temperature range and within the lower range of the residence times. The following may be mentioned as an example of reaction conditions for this purpose: 160°-220° C. and residence times of 0.5-8 seconds, or the catalyst loading which can be calculated from this as the reciprocal.

Conversely, high reaction temperatures, for example 230°-330° C., and longer residence times, for example 5-20 seconds, in conjunction with high molar excesses of alkanol within the said range lead to increased dialkylation on the N-atom.

It is a special advantage of the inventive process that the ratio of N-mono- to N,N-dialkyl-aniline can be formed variably in broad ranges.

Suitable alkanols and dialkyl ethers preferred for this purpose are those having $C_1$-$C_3$ radicals, particularly preferably ethanol and diethyl ether. In this case, the aniline to be alkylated and the alkanol or dialkyl ether are employed in a molar ratio of 1:2-10 (alkanol) or 1:1-5 (ether), preferably 1:3-8 or 1:1.5-4 respectively and particularly preferably 1:3-6 or 1:4-3 respectively, and temperatures of 20020 -320° C., preferably 200°-310° C., are set.

In a further variant of the process according to the invention within the scope of N-dialkylation, a secondary aromatic amine of the formula (II), wherein $R^4$ is other than hydrogen, is alkylated with an alkanol or a corresponding ether, whose radical $R^3$ is different from the radical $R^4$, and tertiary aromatic amines of the formula (I) are thus formed which carry two different alkyl radicals on the N-atom, in addition to the aromatic separated by known methods.

EXAMPLE 1

A reaction tube of about 17 mm internal diameter, suitable for the catalytic gas-phase reaction, was filled with 11.4 g (15 ml) of niobic acid. This niobic acid had been pressed with the addition of 3.5% of graphite to give pellets (d=3 mm). A gas mixture of aniline and methanol in a molar ratio of 1:4 was passed over the catalyst layer at 250° C. at a velocity of 0.65 g/ml.h. The reaction product formed in the course of 65 hours had the following composition, according to gas chromatography:

| Aniline: | 0.1% |
|---|---|
| N-Methylaniline: | 3% |
| N,N-Dimethylaniline: | 95.1% |
| By-products: | 1.8% |

EXAMPLE 2

20 parts by weight of pulverulent niobic acid, 80 parts by weight of $TiO_2$ powder (anatase) and 3 parts by weight of graphite powder were intensively mixed and pressed to give pellets (d=5 mm). A 17 mm wide reaction tube was filled with 15 ml (13.8 g) of the catalyst thus prepared. A gas mixture of aniline and ethanol in a molar ratio of 1:4 was passed over this catalyst layer at 250° C. at a velocity of 0.43 g/ml.h. The reaction mixture formed in the course of 65 hours was condensed and analysed. The following composition of the reaction mixture was found:

| Aniline: | 9.1% |
|---|---|
| N-Ethylaniline: | 46.2% |
| N,N-Diethylaniline: | 43.3% |
| By-products: | 1.4% |

EXAMPLE 3

A 1 1 stirred autoclave was charged with 10 g of pulverulent niobic acid, 189.4 g of aniline and 260.6 g of methanol (molar ratio 1:4). The autoclave was flushed with nitrogen in order to displace the air. It was then pressurised with 5 bar of nitrogen, and the content of the autoclave was heated to 250° C. in the course of one hour. After heating for 1 or 4 hours at 250° C., the reaction mixture showed the following composition:

|  | 1 hour | 4 hours |
|---|---|---|
| Aniline: | 17.7% | 0.7% |
| N-Methylaniline: | 39.3% | 10.3% |
| N,N-Dimethylaniline: | 42.3% | 87.2% |
| By-products: | 0.7% | 1.8% |

EXAMPLE 4

A 1 1 stirred autoclave was charged with 20 g of pulverulent niobic acid, 151 g of aniline and 299 g of ethanol (molar ratio 1:4). After the air had been displaced by nitrogen, the mixture was heated for 6 hours at 220° C. The reaction mixture corresponded to the following composition:

| Aniline: | 56.2% |
|---|---|
| N-Ethylaniline: | 41.5% |
| N,N-Diethylaniline: | 2.0% |
| By-products: | 0.3% |

EXAMPLE 5

For the preparation of N-methylaniline, 0.5 mol each of aniline (47 g) and N,N-dimethylaniline (61 g) and 10 g of pulverulent niobic acid were heated for 4 hours at 250° C. in a 0.25 l shaking autoclave. The analysis of the reduction product showed that considerable transalkylation took place:

| | |
|---|---|
| Aniline: | 32.2% |
| N-Methylaniline: | 24.7% |
| N,N-Dimethylaniline: | 42.9% |
| By-products: | 0.2% |

EXAMPLE 6

In the apparatus as in Example 1, filled with tantalic acid/graphite, a gas mixture of aniline and ethanol in a molar ratio of 1:4 was passed through at 220° C. at a velocity of 0.49 g/ml · h. The reaction mixture formed in the course of 122 hours had the following composition:

| | |
|---|---|
| Aniline: | 38.7% |
| N-Ethylaniline: | 51.6% |
| N,N-Diethylaniline: | 8.7% |
| By-products: | 1.0% |

EXAMPLE 7 CATALYST PREPARATION

A solution of 100 g of tantalum pentachloride in 100 ml of absolute ethanol was introduced as a constant stream into a solution of 100 g of potassium hydroxide in ethanol. After ageing for 24 hours, the precipitate was separated off by means of a suction filter and washed with boiling water until the washing water running off was free of chloride irons.

The precipitate was then kneaded for about 15 minutes in a kneader and then processed in a granulation apparatus to give shaped particles of 1-2 mm diameter. The moist granules were dried at 120° C. and calcined for 3 hours at 300° C. The granules thus obtained showed a BET surface area of 153 m²/g.

EXAMPLES 8 AND 9: ETHYLATION OF ANILINE 20 ml of the hydrated tantalum (V) oxide from Example 7 having a mean particle size of 1-2 mm were introduced into an upright reaction tube of 40 cm length and a diameter of 30 mm. It was possible to temperaturecontrol the reactor by means of an organic heat transfer medium. The temperature in the catalyst bed could be measured by means of a mobile thermocouple. A mixture of aniline and ethanol was metered via a metering device into a vaporiser, converted in the latter into the gas phase and passed over the catalyst. The metering rate was 20 ml/h of liquid mixture; this corresponded to a catalyst loading (LHSV) of 1.0 l/l/h. The reaction product was condensed out and analysed by gas chromatography. The composition of the reaction product by weight is compiled in Table 1.

TABLE 1

| N,N-Diethylation of aniline with ethanol on hydrated tantalum (V) oxide | | | | | | |
|---|---|---|---|---|---|---|
| | Aniline Ethanol | % by weight fractions in the product | | | | Temperature |
| Example | (molar) | Aniline | N-Monoethyl-aniline | N,N-Diethyl-aniline | Remainder | (°C.) |
| 8 | 1:4 | 3.6 | 47.8 | 47.8 | 0.8 | 290 |
| 9 | 1:6 | 3.7 | 37.7 | 56.3 | 2.3 | 290 |

After a running period of 90 hours, the result is unchanged

EXAMPLE 10

Pulverulent niobic acid of type AD/620 from Messrs Companhia Brasileira de Metalurgia e Mineracao was, after admixture of 3.5 % of graphite, pressed to give pellets (d=5 mm).

A 17 mm wide reaction tube was filled with 17.4 g (15 ml) of the pelleted niobic acid. A mixture of aniline and ethanol in a molar ratio of 1:4 was passed over this catalyst layer at 230° C. under atmospheric pressure at a velocity of 0.45 g/ml*h. The reaction mixture formed in the course of 191 hours was condensed and analysed. This gave the following composition of the reaction product.

| | |
|---|---|
| Aniline: | 1.2% |
| N-Ethylaniline: | 24.6% |
| N,N-Diethylaniline: | 71.3% |
| By-products: | 2.9% |

EXAMPLES 11-15

In a tubular reactor with 1 l niobic acid as catalyst and with a feed of 4 mols of ethanol and 1 mol of aniline (according to gas chromatography (GC) analysis 48.9% of aniline and 51.1% of ethanol, determined as plane percents) the following figures were obtained at the different temperatures and catalyst loadings as mentioned:

TABLE 2

| (Examples 11-15) | | | | | | | | | | | |
|---|---|---|---|---|---|---|---|---|---|---|---|
| No. | Temp. °C. | GHSV 1/l.h | Product analysis | | | GC plane % | | | Aniline transformation (%) | Selectivity in mol % | |
| | | | DEE | EtOH | An. | MEA | DEA | NAA | | MEA | DEA |
| 11 | 270 | 0,30 | 4,6 | 6,4 | 0,3 | 19,6 | 57,8 | 9,9 | 99,5 | 26,3 | 62,9 | 89,2 |
| | 280 | 0,30 | 6,7 | 5,7 | 0,4 | 20,3 | 46,6 | 18,5 | 99,3 | 27,7 | 51,7 | 79,5 |
| | 290 | 0,30 | 6,7 | 3,8 | 1,1 | 25,7 | 34,8 | 26,2 | 98,1 | 34,2 | 37,6 | 71,7 |
| | 300 | 0,30 | 5,2 | 2,6 | 2,2 | 29,2 | 26,0 | 31,5 | 96,4 | 38,5 | 27,8 | 66,3 |
| | 310 | 0,30 | 4,3 | 1,7 | 3,6 | 31,0 | 18,9 | 39,0 | 94,3 | 39,7 | 19,7 | 59,4 |
| 12 | 270 | 0,50 | 3,1 | 8,6 | 0,9 | 23,5 | 58,1 | 4,9 | 98,5 | 31,5 | 63,2 | 94,7 |
| | 280 | 0,50 | 4,1 | 8,4 | 0,8 | 23,5 | 55,1 | 6,9 | 98,6 | 31,8 | 60,6 | 92,4 |
| | 290 | 0,50 | 4,9 | 6,3 | 0,7 | 24,4 | 50,5 | 11,9 | 98,8 | 32,5 | 54,6 | 87,1 |
| | 300 | 0,50 | 5,4 | 5,0 | 1,1 | 27,1 | 42,6 | 17,2 | 98,1 | 35,8 | 45,7 | 81,5 |
| | 310 | 0,50 | 5,1 | 3,3 | 2,0 | 30,0 | 31,8 | 26,1 | 96,7 | 39,0 | 33,5 | 72,5 |
| 13 | 270 | 0,75 | 2,7 | 10,5 | 1,3 | 24,5 | 56,1 | 4,1 | 97,7 | 33,4 | 62,1 | 95,5 |

TABLE 2-continued (Examples 11-15)

| No. | Temp. °C. | GHSV 1/l.h | Product analysis | | | GC plane % | | | Aniline transformation (%) | Selectivity in mol % | | |
|---|---|---|---|---|---|---|---|---|---|---|---|---|
| | | | DEE | EtOH | An. | MEA | DEA | NAA | | MEA | DEA | |
| | 280 | 0,75 | 3,8 | 8,9 | 0,9 | 23,1 | 55,8 | 6,6 | 98,4 | 31,3 | 61,4 | 92,7 |
| | 290 | 0,75 | 4,2 | 7,7 | 1,0 | 24,6 | 50,9 | 10,5 | 98,3 | 33,0 | 55,5 | 88,5 |
| | 300 | 0,75 | 5,1 | 5,8 | 1,0 | 26,0 | 44,9 | 15,7 | 98,3 | 34,6 | 48,5 | 83,0 |
| | 310 | 0,75 | 5,0 | 4,3 | 1,6 | 29,3 | 36,8 | 21,5 | 97,4 | 38,2 | 39,0 | 77,2 |
| 14 | 270 | 1,00 | 2,3 | 17,8 | 3,2 | 26,8 | 46,7 | 2,6 | 94,1 | 40,1 | 56,7 | 96,8 |
| | 280 | 1,00 | 3,0 | 11,4 | 2,0 | 26,0 | 52,0 | 4,6 | 96,5 | 36,1 | 58,7 | 94,8 |
| | 290 | 1,00 | 4,1 | 9,0 | 1,4 | 25,0 | 51,6 | 7,4 | 97,6 | 34,3 | 57,5 | 91,8 |
| | 300 | 1,00 | 5,0 | 7,5 | 1,1 | 25,6 | 48,0 | 11,1 | 98,1 | 34,8 | 53,0 | 87,8 |
| | 310 | 1,00 | 5,6 | 5,9 | 1,5 | 27,6 | 41,6 | 16,3 | 97,5 | 37,0 | 45,3 | 82,3 |
| 15 | 270 | 1,50 | 3,2 | 39,6 | 5,4 | 27,6 | 22,2 | 1,6 | 87,0 | 58,8 | 38,4 | 97,2 |
| | 280 | 1,50 | 3,3 | 23,0 | 4,3 | 25,5 | 40,2 | 2,8 | 91,5 | 42,2 | 54,0 | 96,2 |
| | 290 | 1,50 | 4,2 | 12,2 | 2,7 | 26,2 | 48,0 | 5,4 | 95,2 | 37,7 | 56,0 | 93,7 |
| | 300 | 1,50 | 5,0 | 9,3 | 2,0 | 26,0 | 46,5 | 9,4 | 96,5 | 36,4 | 52,9 | 89,3 |
| | 310 | 1,50 | 5,3 | 7,7 | 1,9 | 27,4 | 43,0 | 12,4 | 96,7 | 37,9 | 48,2 | 86,1 |

GHSV (Gaseous Hourly Space Velocity) = Catalyst loading in 1/l.h
DEE Diethylether
EtOH Ethanol
An. Aniline
MEA Mono-N-ethylaniline
DEA Di-N-ethylaniline
NAA nucleus-alkylated anilines

What is claimed is:

1. A process for the preparation of aromatic amines, alkylated on the N-atom, from aromatic amines and lower alcohols, said aromatic amines being selected from the group consisting of aniline, 1-napthylamine, o-, m- and p-toluidine, o-, m- and p-ethylaniline, the isomeric xylidines 2,3-, 2,4-, 2,5-, 2,6-, 3,4-and 3,5-dimethylaniline and 4-methyl-1-naphthylamine, wherein the reaction is carried out in the presence of niobic acid or tantalic acid at a temperature of from 160° to 400° C.

2. The process for the preparation of aromatic amines of the formula

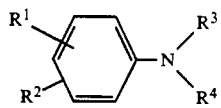

wherein
$R^1$ represents hydrogen, methyl or ethyl,
$R^2$ represents hydrogen or methyl, or
$R^1$ and $R^2$ together denote a fused benzene ring which can be substituted by methyl, and
$R^3$ represents $C_1$ to $C_6$ alkyl,
$R_4$ represents hydrogen or $C_1$ to $C_{10}$ alkyl,
by reacting aromatic amines of the formula

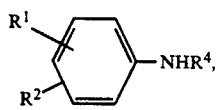

with alkanols of the formula $R^3OH$ or the corresponding ethers of the formula $R^3$—O—$R^3$, $R^1$, $R^2$, $R^3$ and $R^4$ having the above meaning, or by reacting aromatic amines of the formula

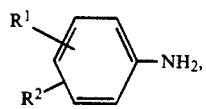

with aromatic amines of the formula

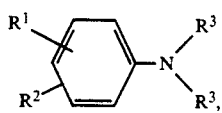

$R^1$, $R^2$ and $R^3$ having the above meaning, in the gas phase or liquid phase at an elevated temperature of claim 1, wherein the reaction is carried out in the presence of niobic acid or tantalic acid at 160°–400° C.

3. The process of claim 2, wherein the reaction is carried out at 200°–300° C.

4. The process of claim 2, wherein for the preparation of N,N-dialkyl anilines the reaction in the gas phase is carried out at 230°–330° C.

5. The process of claim 1, wherein the niobic acid or tantalic acid is mixed in a weight ratio of from 5:95 to 99:1 with an inert solid and the mixture is pelletised.

6. The process of claim 5, wherein the niobic acid or tantalum acid is mixed in a weight ratio of from 50:50 to 98:2 with an inert solid and the mixture is pelletised.

7. The process of claim 5, wherein the inert solid is titanium dioxide, zinc oxide, iron oxide or α-alumina.

8. The process of claim 2, wherein, in the case of reaction in the gas phase, a catalyst loading of 0.1–4 l/l/h of aromatic amine to be alkylated per liter of catalyst per hour is set.

9. The process of claim 8, wherein a catalyst loading of 0.3–2 l/l/h is set.

10. The process of claim 2, wherein, in the case of reaction in the liquid phase, niobic acid or tantalic acid is used in a quantity of 2%–25% by weight, relative to the aromatic amine to be alkylated.

11. The process of claim 10, wherein niobic acid or tantalum acid is used in a quantity of 4%–20% by weight, relative to the aromatic amine to be alkylated.

12. The process of claim 2, wherein 0.3–20 mols of alkanol per mol of the aromatic amine are employed and in the case of the corresponding ethers 1 mol of the ether is to be equated with 2 mols of the alkanol.

13. The process of claim 2, wherein the reaction is carried out at 160°–220° C. for preferential N-monoalkylation as against N,N-dialkylation.

14. The process for the preparation of aromatic amines, dialkylated on the N-atom, of claim 1, wherein the reaction is carried out at 200°–320° C. and with a molar ratio of aniline to alkanol or the corresponding dialkyl ether of 1:2–10 or 1:1–5 respectively.

15. The process of claim 14, wherein the dialkylated aromatic amines to be prepared are diethylated amines.

16. The process of claim 14, wherein the reaction is carried out at 220°–310° C.

17. The process of claim 1, wherein the catalyst has a BET surface area of 5–350 $m^2/g$.

18. The process of claim 17, wherein the catalyst has a BET surface area of 50–350 $m^2/g$.

19. The process of claim 18, wherein the catalyst has a BET surface area of 100–250 $m^2/g$.

20. The process of claim 19, wherein the catalyst has a BET surface area of 100–200 $m^2/g$.

* * * * *